United States Patent
Mae et al.

(10) Patent No.: US 7,090,874 B2
(45) Date of Patent: Aug. 15, 2006

(54) LIGAND FOR PEROXISOME PROLIFERATOR-ACTIVATED RECEPTOR

(75) Inventors: Tatsumasa Mae, Kakogawa (JP); Misuzu Tsukagawa, Akashi (JP); Hideyuki Kishida, Kakogawa (JP); Mitsuaki Kitano, Takasago (JP); Mikio Kitahara, Kobe (JP); Kaku Nakagawa, Kyoto (JP); Minpei Kuroda, Tokyo (JP); Yoshihiro Mimaki, Hachioji (JP); Yutaka Sashida, Hachioji (JP)

(73) Assignee: Kaneka Corporation, Osaka (JP)

( * ) Notice: Subject to any disclaimer, the term of this patent is extended or adjusted under 35 U.S.C. 154(b) by 8 days.

(21) Appl. No.: 10/752,643

(22) Filed: Jan. 8, 2004

(65) Prior Publication Data

US 2004/0253329 A1     Dec. 16, 2004

Related U.S. Application Data

(63) Continuation of application No. 10/277,967, filed on Oct. 23, 2002, now abandoned.

(30) Foreign Application Priority Data

Oct. 23, 2001   (JP) .............................. 2001-324414

(51) Int. Cl.
*A61K 36/9066*     (2006.01)
(52) U.S. Cl. ...................... 424/756; 424/725
(58) Field of Classification Search ................. 424/756
See application file for complete search history.

(56) References Cited

FOREIGN PATENT DOCUMENTS

| JP | 11-246399 | * | 9/1999 |
| JP | 2000-355538 | | 12/2000 |
| WO | WO 99/22728 | * | 5/1999 |

OTHER PUBLICATIONS

Akira Asai and Teruo Miyazawa, "Dietry Curcuminoids Prevent High-Fat Diet-Induced Lipid Accumulation In Rat Liver and Epididymal Adipose Tissue", American Society for Nutritional Sciences, pp. 2932-2935, 2001.

* cited by examiner

*Primary Examiner*—Susan D. Coe
(74) *Attorney, Agent, or Firm*—Kenyon & Kenyon LLP

(57) ABSTRACT

The object of the present invention is to provide PPARγ ligand derived from naturally occurring sources and a composition for preventing and/or improving Insulin Resistance Syndrome, diabetes mellitus, obesity or visceral fat obesity comprising the PPARγ ligand as an active agent.

The present invention relates to a ligand for peroxisome proliferator-activated receptor
which comprises curcumin or its derivatives.

The composition according to the present invention, which comprises the PPARγ ligand as an active agent is useful for preventing and/or improving Insulin Resistance Syndrome, diabetes mellitus, obesity or visceral fat obesity.

4 Claims, No Drawings

LIGAND FOR PEROXISOME PROLIFERATOR-ACTIVATED RECEPTOR

CROSS REFERENCE TO RELATED APPLICATION

This application is a continuation application of patent application Ser. No. 10/277,967 filed on Oct. 23, 2002, now abandoned, which is incorporated herein in its entirety by reference thereto.

BACKGROUND OF THE INVENTION

The present invention relates to a ligand for peroxisome proliferator-activated receptor, and a composition for preventing and/or improving Insulin Resistance Syndrome (e.g., type-II diabetes mellitus, hyperinsulinemia, dyslipidemia, obesity, hypertension and arteriosclerotic cardiovascular disease) comprising the ligand for peroxisome proliferator-activated receptor as an active agent.

PRIOR ART

Peroxisome proliferator-activated receptor (PPAR) is a ligand-dependent transcriptional regulatory factor belonging to the nuclear receptor family, which has been identified as a transcriptional regulatory factor that regulates expression of a group of genes that maintain lipid metabolism. It is known that three subtypes of PPAR, i.e., PPARα, PPARδ (PPARβ, NUC-1, FAAR) and PPARγ, have been identified in mammals. PPARα is mainly expressed in the liver while PPARδ is ubiquitously expressed. PPARγ has two isoforms, PPARγ1 and PPARγ2. PPAγ1 is expressed not only in adipose tissues but also in immune system organs, adrenals and small intestine. PPARγ2 is specifically expressed in adipose tissues, and is a master regulator which regulates differentiation/maturation of adipocytes (TeruoKawada, IgakunoAyumi. (Journal of Clinical and Experimental Medicine) 184, 519–523, 1998).

Examples of known PPARγ ligands include: arachidonic acid metabolites such as 15-deoxy-Δ12, 14-prostaglandin J2 and Δ12-prostaglandin J2;.unsaturated fatty acids such as ω-3-polyunsaturated fatty acid, α-linolenic acid, eicosapentaenoic acid (EPA) and docosahexaenoic acid.(DHA); and eicosanoids such as 9-hydroxy-octadecadienoic acid and 13-hydroxy-octadecadienoic acid (J. Auwerx, Diabetologia, .42, 1033–1049, 1999). It has been also disclosed that PPARγ ligands include $C_{10-26}$ conjugated-unsaturated fatty acids having a conjugated-triene or tetraene structure (Japanese Patent Application 2000-355538). It is also known that examples of synthetic PPARγ ligands include thiazolidinediones such as troglitazone,. pioglitazone and rosiglitazone.

It has been suggested that thiazolidinediones, which are PPARγ ligands, are associated with improvement of insulin resistance since their agonistic activities correlates with their hypoglycemic actions. Based on these findings, they were developed as drugs for improving insulin resistance against type-II diabetes mellitus (non-insulin dependent diabetes mellitus: NIDDM). Namely, a thiazolidinedione, which is one of PPARγ ligands, can improve insulin resistance by activating PPARγ to increase number of small adipocytes with normal function differentiated from preadipocytes and to decrease number of large adipocytes, which hyperproduce and/or hypersecrete factors causing insulin resistance such as TNFα and free fatty acid, by apoptosis (A. Okuno, et al., Journal of Clinical Investigation, 101,1354–1361,1998). PPARγ ligands are also useful for prevention and/or improvement. of Insulin Resistance Syndrome, not only for type-II diabetes mellitus but also for hyperinsulinemia, dyslipidemia, obesity, hypertension and arteriosclerotic cardiovascular disease (R. A. DeFronzo, et al., Diabetes Care, 14, 173–194, 1991), due to its ability to improve insulin resistance. As for the effect against obesity, it has been reported that administration of troglitazone to type-II diabetic patients reduces visceral fat in the patients (I. E. Kelly, et al., Diabetes Care, 22, 288–293, 1999; Y. Mori, et al., Diabetes Care, 22, 908–912, 1999). Thus, PPARγ ligands are also useful for prevention and/or improvement of visceral fat obesity.

Curcumin and its derivatives are components contained in tropical or subtropical plants, of which a good representative is perennial *Curcuma longa,* belonging to Zingiberaceae. *Curcuma longa* is generally known as turmeric, one of spices which are used in curry, and can be used not only for foods, but also as a colorant in food or clothing, or as a herbal medicine in traditional therapies such as Chinese medicine (Kampo), Indian Ayurveda and Indonesian Jamu due to its hemostatic, stomachic, antibacterial and anti-inflammatory actions.

It has been proved that curcumin has various physiological activities such as anti-oxidative action, cholagogic action, the internal organs (hepatic or pancreatic) function-potentiating action, carcinogenesis-inhibiting action, lipid metabolism-improving action, and whitening action. P. Suresh Babu and K. Srinivasan reported that streptozotocin-induced diabetic rats, which were maintained on diet containing 0.5% curcumin, exhibited reduced cholesterol, triglyceride and phospholipid levels in blood (Molecular and Cellular Biochemistry, 166, 169–175, 1997) and amelioration of renal lesions associated with diabetes mellitus (Molecular and Cellular Biochemistry, 181, 87–96, 1998). Japanese Patent Application Hei-11-246399 discloses that enhanced activity of acyl-CoA oxidase (β-oxidation promotive enzyme) and inhibition of triglyceride accumulation in the liver were observed in rats which received curcumin. However, it has not been known that curcumin and/or its derivatives are PPARγ ligands and have hypoglycemic or visceral fat-reducing action.

As described above, PPARγ ligands can improve insulin resistance and prevent and/or improve Insulin Resistance Syndrome such as type-II diabetes mellitus, hyperinsulinemia, dyslipidemia, obesity (particularly visceral fat obesity), hypertension and arteriosclerotic cardiovascular disease. Accordingly, the object of the present invention is to provide a PPARγ ligand derived from naturally occurring sources and a composition comprising the PPARγ ligand as an active agent for preventing and/or improving Insulin Resistance Syndrome, diabetes mellitus, obesity or visceral fat obesity.

SUMMARY OF THE INVENTION

The present inventors found that Curcuma extract has hypoglycemic action and that, after intense studies, particular components contained in *Curcuma* (curcumin and its derivatives) have PPARγ ligand activities. They also found that these particular components have hypoglycemic action and visceral fat-reducing action. The present invention was developed based on these findings.

In summary, the present invention relates to a ligand for peroxisome proliferator-activated receptor which comprises curcumin or its derivative.

The present invention also relates to a composition for preventing and/or improving Insulin Resistance Syndrome, diabetes mellitus, or obesity or visceral fat obesity which comprises at least one selected from the group consisting of curcumin and its derivatives as an active agent.

DESCRIPTION OF THE PREFERRED EMBODIMENTS

The present invention will be described in more detail referring to the following embodiments. The PPARγ ligand according to the present invention comprises curcumin or its derivative. A composition comprising, as an active agent, at least one selected from the group consisting of curcumin and its derivatives according to the present invention has hypoglycemic action and visceral fat-reducing action, and therefore be useful to prevent and/or improve Insulin Resistance Syndrome, diabetes mellitus, obesity or visceral fat obesity.

Curcumin to be used in the present invention is 1,7,-bis (4-hydroxy-3-methoxyphenyl)-1,6-heptadiene-3,5-dione, and curcumin derivatives (curcuminoids) include, for example, demethoxycurcumin, bisdemethoxycurcumin, dihydrocurcumin, tetrahydrocurcumin, hexahydrocurcumin, dihydroxytetrahydrocurcumin, Yakuchinone A and. Yakuchinone B, and their salts, oxidants, reductants, glycosides and esters thereof. Those may be purified from plants or chemically synthesized compounds. Plant-derived curcumin and/or its derivatives can be obtained by extraction from plants including Zingiberaceae*Curcuma*, such as *Curcuma longa*(turmeric), *Curcuma aromatica*(wild turmeric), *Curcuma zedoaria* (zedoary), *Curcuma xanthorrhiza*, mango ginger, Indonesian arrowroot, yellow zedoary, black zedoary and galangal.

Any conventional method can be used to prepare curcumin and its derivatives to be used in the present invention. For example, turmericoleoresin, a food additive, which essentially contains curcumin, can be produced by extracting from a dry product of rhizome,of turmeric with ethanol at an elevated temperature, with hot oil and fat or propylene glycol, or with hexane or acetone at from room temperature to a high temperature. Alternatively, those can be produced by the methods disclosed in Japanese Patent Application 2000-236843, Japanese Patent Application Hei-11-235192 and Japanese Patent Application Hei-6-9479, and Japanese Kohyo Publication Hei-11-502232 and Japanese Kohyo Publication Hei-9-503528. According to the present invention, a purified product of at least one selected from the group consisting of curcumin and its derivatives may be used. Alternatively, a semi-purified or crude product thereof may be used, provided that it does not contain impurities which may not be acceptable as a pharmaceutical or food product.

A composition for preventing and/or improving Insulin Resistance Syndrome, diabetes mellitus, obesity or visceral fat obesity according to the present invention may comprise a PPARγ ligand, and is the composition comprises, as an active agent, at least one selected from the group consisting of curcumin and its derivatives. The compositions of the invention may be used in, for example, but not limited to, foods and drinks including foods with health claims (e.g., foods for specified health uses or foods for nutrient function claims) or health foods, pharmaceuticals and quasi drugs.

When used as foods and drinks, the inventive compositions may be administered alone,. or formulated in combination with any known carrier(s) and/or additive(s) into any suitable dosage form including, for example, capsules, tablets and granules. The PPARγ ligand according to the present invention may be present in such formulations at an amount of 0.1 to 100% by weight, and preferably 10 to 90% by weight. Alternatively, the inventive composition may be added to any kinds of foods and drinks, including: confectionery such as chewing gums, chocolates, candies, jellies, biscuits or crackers; frozen desserts such as an ice cream or ice cube; drinks such as tea, soft drinks, nutritional supplement drinks or beauty supplement drinks; noodles such as udon noodle, Chinese noodle, spaghetti or instant noodle; foods made from fish paste such as boiled fish paste (kamaboko), tube-shaped fish paste cake (chikuwa) or a cake of pounded fish (hanpen); dressing, mayonnaise, sauce or other seasonings; fat foods such as margarine, butter or salad oil; bread; ham; soup; boil-in-bag foods; and frozen foods. A food or drink containing the inventive composition may be given to a human at a dose of 0.1 to 3000 mg/kg body weight/day (based on inventive PPARγ ligand) for an adult, and preferably 1 to 300 mg/kg body weight/day (based on the PPARγ ligand). The inventive composition may be also used as a feed for a domestic animal or pet-food for a pet. In this case, a feed or food containing the inventive composition may be preferably given at a dose of 0.1 to 3000 mg/kg body weight/day (based on the PPARγ ligand).

When used as pharmaceuticals, the inventive compositions may be formulated into any suitable do sage forms for administration including, but not limited to, capsules, tablets, granules, injection solution, suppositories and patches. In preparation of the drugs, such formulations comprising the inventive composition may additionally comprise other pharmaceutically acceptable additive (s) such as an excipient, a disintegrator, a lublicant, a binder, an anti-oxidant, a colorant, an anti-aggregation agent, a sorbefacient, a solubilizer and/or a stabilizer as appropriate. Such a formulation may be administered to a human at a dose of 0.1 to 3000 mg/kg body weight/day (based on inventive PPARγ ligand) for an adult, and preferably 1 to 300 mg/kg body weight/day (based on PPARγ ligand), once or divided into several times a day. The inventive composition may be also administered to a domestic animal or a pet as a pharmaceutical drug. In this case, a formulation containing the inventive composition may be preferably administered at a dose of 0.1 to 3000 mg/kg bodyweight/day (based on the inventive PPARγ ligand).

According to the present invention, a ligand for peroxisome proliferator-activated receptory (PPARγ) and a composition comprising the same are provided. The composition according to the present invention is useful for preventing and/or improving Insulin Resistance Syndrome, diabetes mellitus, obesity or visceral fat obesity.

EXAMPLES

The present invention will be described in more detail by referring to the following Examples though the present invention is not limited to these Examples.

Example 1

Extraction and Isolation of Compounds from *Curcuma longa*

*Curcuma longa* powder (1.0 kg) was extracted with ethanol (8.0 L) at room temperature in darkness for 2 days and filtered to give an extracted solution. The solvent was removed from the extracted solution by vacuum concentration to give an extract (118 g). The extract was then subjected to porous ion-exchange resin DIAION HP-20 column chromatography (1600 ml), and eluted sequentially with 30% methanol, 50% methanol and 80 % methanol (1.5

L each), and then methanol, ethanol and ethyl acetate (3 L each) to give 6 fractions (fractions 1, 2, 3, 4, 5 and 6). Purification was performed by repeatedly subjecting fraction 4 (63.5 g) to silica gel chromatography A (eluant; hexane: acetone=2:1→3:2→4:3, v/v) and silica gel chromatography B (eluant; chloroform: acetone=99:1→19:1, v/v) to give compound 1 (6.4 g), compound 2 (1.2 g) and compound 3 (1.1 g).

Structure analysis showed that compounds 1 to 3,were known compounds: compound 1 was identified as curcumin, compound 2 was demethoxycurcumin and compound 3 was bisdemethoxycurcumin, respectively. The structures of these compounds were identified based on the spectrum data described in the report by M. Kuroyanagi et al. (Yakugaku Zassi (Journal of Pharmaceuticals Society of Japan), 90,1467–1470, 1970). Structural formulae of compounds 1 to 3 are shown in Table 1 below.

mouse PPARγ ligand binding domain gene (amino acid sequences 174 to 475). The 4×UASg-luc is a reporter plasmid incorporated luciferase gene with 4-time-repeated responsive element (UASg) of GAL4 ligated thereto at the upstream end thereof. At approximately 24 hours after the transfection, the medium was replaced by a medium containing each sample (n=4) and cells were incubated for an additional 2 hours. Each sample used was dissolved in dimethyl sulfoxide (DMSO) and DMSO was used as an untreated control sample. These samples were added to medium at a volume ratio of 1/1000. Cells were washed with Ca, Mg-containing phosphate buffered saline (PBS+) and added with LUCLITE™ (product of Packard), a reagent for determination of luminescence using luciferase. Then, the luminescent intensity by expressed luciferase was determined in a TOPCOUNT™ Microplate Scintillation/Luminescence Counter (product of Packard).

TABLE 1

| Compound No. | Compound Name | Structural Formula |
|---|---|---|
| Compound 1 | Curcumin | |
| Compound 2 | Demethoxycurcumin | |
| Compound 3 | Bisdemethoxycurcumin | |

Example 2

PPARγ Ligand Activity

CV-1 cells (cultured cells derived from male African green monkey kidney) were inoculated into a 96-well culture plate at $6 \times 10^3$ cells/well, and incubated at 37° C. for 24 hours under 5% $CO_2$ conditions. As a medium, DMEM (Dulbecco's Modified Eagle Medium, product of GIBCO) containing 10% FBS (fetal bovine serum), 10 ml/L penicillin-streptomycin (5000 IU/ml and 5000 μg/ml, respectively, product of GIBCO), 37 mg/L ascorbic acid (product of Wako Pure Chemical Industries, Ltd.) was used. Cells were washed with OPTI-MEM (product of GIBCO), a serum-free medium, and transfected with pM-mPPARγ and 4×USAg-luc using LIPOFECTAMINE PLUS™ (product of GIBCO), a reagent for transfection of genes using a cationic lipid. The pM-mPPARγ is a plasmid for chimeric protein expression which consisted of a yeast-derived transcription factor GAL4 gene (amino acid sequences 1 to 147) ligated to a The luminescent intensity was determined in the control group in the same way as in the test groups, but using pM (a plasmid lacking PPARγ ligand binding domain gene) instead of pM-mPPARγ. The ratio (test group/control group) of the average luminescent intensity between the test and control groups (n=4) was determined for each sample, and the relative activity of test sample. against the untreated control sample was determined as the PPARγ ligand activity of the sample. The results are shown in Table 2 below.

TABLE 2

| | Added Concentration | PPARγ ligand activity |
|---|---|---|
| Untreated Control (DMSO) | (0.1%) | 1.00 |
| Troglitazone | 0.5 μM | 2.37 ± 0.24 |
| | 1 μM | 4.26 ± 0.22 |
| | 2 μM | 6.93 ± 0.56 |

TABLE 2-continued

| | Added Concentration | PPARγ ligand activity |
|---|---|---|
| Compound 1 (Curcumin) | 2 μg/ml (5.4 μM) | 2.36 ± 0.94 |
| | 5 μg/ml (13.6 μM) | 3.67 ± 1.06 |
| | 10 μg/ml (27.2 μM) | 4.16 ± 1.10 |
| Compound 2 (Demethoxycurcumin) | 2 μg/ml (5.9 μM) | 2.17 ± 0.39 |
| | 5 μg/ml (14.8 μM) | 4.25 ± 0.77 |
| | 10 μg/ml (29.6 μM) | 4.41 ± 0.35 |
| Compound 3 (Bisdemethoxycurcumin) | 2 μg/ml (6.5 μM) | 1.88 ± 0.33 |
| | 5 μg/ml (16.2 μM) | 3.55 ± 0.38 |
| | 10 μg/ml (32.5 μM) | 4.08 ± 0.46 |

(Mean ± SD)

PPARγ ligand activity of each test compound was compared with that of troglitazone (product of Sankyo) used as a positive control.

It is apparent from Table 2 that curcumin, demethoxycurcumin and bisdemethoxycurcumin exhibited concentration-dependent PPARγ ligand activities.

Example 3

The Effect of the Compound in Model Mice of Type-II Diabetes Mellitus

KK-Ay mice, a model of genetically obese and type-II diabetic animals, were used to evaluate the effect of curcumin. Pioglitazone, a drug for treating diabetes mellitus, was used as a positive control.

KK-Ay mice (females, 6 weeks old) were divided into 3 groups (5 animals per group). By using a normal diet (product of Oriental Yeast Co. Ltd., Table 3) as a base feed, three types of feeds, i.e., a diet with out any additives, with pioglitazone and with curcumin, were prepared. Mice were placed in an environment in which they were freely accessible to a diet without any additives (control group), with pioglitazone (pioglitazone-added group) or with curcumin (curcumin-added group) for 4 weeks. Pioglitazone used was obtained by grinding Actos tablet 30 (30 mg pioglitazone per tablet, Takeda Chemical Industries Ltd.) in an agate mortar. The ground Actos tablet was then added to the normal diet at a dose of 0.04% pioglitazone. Curcumin was added to the normal diet at a dose of 0.5% curcumin.

TABLE 3

| | | Normal diet (AIN-93G modified) |
|---|---|---|
| Ratio | Fat | 22% |
| | Carbohydrate | 58.5% |
| | Protein | 19.5% |
| Total energy | | 4,100 kcal/kg |
| Formulation | Casein | 20.000% |
| | Cornstarch | 49.948% |
| | Sucrose | 10.000% |
| | Soybean oil | 10.000% |
| | Cellulose powder | 5.000% |
| | AIN-93 mineral mixture | 3.500% |
| | AIN193 vitamin mixture | 1.000% |
| | Choline bitartrate | 0.250% |
| | Tertiary butylhydroquinone | 0.002% |
| | L-cystine | 0.300% |

During feeding, a small amount of blood was collected from the caudal vein of mice every week to determine blood glucose level using a simple bloodglucose level analyzer GLUTESTACE (Sanwa Kagaku Kenkyusho Co., Ltd.).

The mouse body weights are shown in Table 4. The mouse body weights in both pioglitazone-added and curcumin-added groups changed in a similar pattern of control group (without any additives) without any significant difference.

TABLE 4

| | Mouse Body weight (g) | | |
|---|---|---|---|
| | Control group (without any additives) | Pioglitazone-added group | Curcumin-added group |
| Start | 27.3 ± 0.3 | 26.9 ± 1.0 | 25.5 ± 0.7 |
| After 1 week | 34.5 ± 0.9 | 36.7 ± 1.0 | 34.7 ± 1.1 |
| After 2 weeks | 38.9 ± 1.1 | 39.9 ± 1.2 | 39.8 ± 0.7 |
| After 3 weeks | 41.0 ± 1.3 | 42.3 ± 1.2 | 42.8 ± 0.9 |
| After 4 weeks | 43.5 ± 1.3 | 43.8 ± 1.4 | 44.7 ± 1.0 |

(Mean ± SD)

Blood glucose levels are shown in Table 5 below. When feeding started, mice had a blood glucose level of 139 to 151 mg/dl, and hyperglycemia was not observed in any groups. Mice of the control group (without any additives) showed elevated blood glucose level, indicating development of diabetes mellitus. Elevation of blood glucose level observed in the mice of the group which received pioglitazone (a drug for treating diabetes mellitus) was suppressed significantly, compared with that of the control group (without any additives), indicating potent hypoglycemic action of pioglitazone. In the curcumin group, the elevation of blood glucose level was also suppressed significantly, indicating that. curcumin has hypoglycemic action.

TABLE 5

| | Blood Glucose Level (mg/dl) | | |
|---|---|---|---|
| | Control group (without any additives) | Pioglitazone-added group | Curcumin-added group |
| Start | 142 ± 12 | 151 ± 9 | 139 ± 7 |
| After 1 weeks | 322 ± 70 | 163 ± 23** | 191 ± 18** |
| After 2 weeks | 427 ± 70 | 182 ± 9** | 222 ± 46** |
| After 3 weeks | 455 ± 66 | 166 ± 18** | 348 ± 125 |
| After 4 weeks | 479 ± 71 | 153 ± 21** | 344 ± 105* |

(Mean ± SD;
*$p < 0.05$;
**$p < 0.01$)

Example 4

The Effect of the Compound in Model Mice of Diet-induced Obesity

C57BL/6J mice (females, 8 weeks old) were freely accessible to a high fat/high sugar diet (Oriental Yeast Co., Ltd., Table 6) for 8 weeks to obtain dietary obese animals. By using a normal diet (Oriental Yeast Co. Ltd., Table 3) as a base feed, two types of feeds, i.e., a diet without any additives and with 0.5% curcumin, were prepared. Next, said mice were divided into 2 groups (7 animals per group), and each group was freely accessible to a diet without any additives (control group) or with 0.5% curcumin (curcumin group) for 4 weeks. After an overnight fasting, mice were subjected to abdominal section under ether anesthesia to collect blood from the abdominal aorta, and then sacrificed. Then, adipose tissues were collected from the tissues around uterus, kidney and mesentery, and their weights were determined. The sum of the weights of periuterine, perirenal and mesenteric adipose tissues was determined as the total amount of intra-abdominal adipose tissue. The results are shown in Table 7.

TABLE 6

|  |  | High fat/High sugar divisional diet |
| --- | --- | --- |
| Ratio | Fat | 53% |
|  | Carbohydrate | 27% |
|  | Protein | 20% |
| Total energy |  | 5,100 kcal/kg |
| Formulation | Casein | 25.000% |
|  | Cornstarch | 14.869% |
|  | Sucrose | 20.000% |
|  | Soybean oil | 2.000% |
|  | Lard | 14.000% |
|  | Beef tallow | 14.000% |
|  | Cellulose powder | 5.000% |
|  | AIN-93 mineral mixture | 3.500% |
|  | AIN193 vitamin mixture | 1.000% |
|  | Choline bitartrate | 0.250% |
|  | Tertiary butylhydroquinone | 0.006% |
|  | L-cystine | 0.375% |

TABLE 7

|  | Control group (without any additives) | Curcumin-added group |
| --- | --- | --- |
| Diet intake amount (g/day/animal) | 3.16 ± 0.58 | 3.24 ± 0.55 |
| Body weight after feeding (g) | 24.4 ± 2.5 | 22.9 ± 0.9 |
| Adipose tissue per body weight (% by weight) |  |  |
| Periuterine adipose tissue (a) | 1.64 ± 0.82 | 0.8 ± 0.21** |
| Perirenal adipose tissue (b) | 0.86 ± 0.50 | 0.46 ± 0.15* |
| Mesenteric adipose tissue (c) | 0.75 ± 0.43 | 0.39 ± 0.11* |
| Intra-abdominal adipose tissue (a + b + c) | 3.25 ± 1.73 | 1.65 ± 0.42** |

(Mean ± SD;
*$p < 0.05$;
**$p < 0.01$)

It is apparent from Table 7 that no significant difference was detected in diet intake amount or body weight between the curcumin group and the control group (without any additives) while the curcumin group exhibited significantly reduced the weights of periuterine, perirenal, mesenteric and intra-abdominal adipose tissues when compared with those of the control group. In other words, it was proved that intake of curcumin-containing food reduces the visceral fat accumulated by taking high-fat/high sugar diet.

Example 5

Preparation of Curcumin-containing Tablets

| Curcumin | 45 parts by weight |
| --- | --- |
| Lactose | 35 parts by weight |
| Crystalline cellulose | 15 parts by weight |
| Sucrose fatty acid ester | 5 parts by weight |

Curcumin-containing tablets for foods were prepared using the above-listed ingredients according to a conventional method.

Example 6

Preparation of Curcumin-containing Soft Capsules

| Curcumin | 40 parts by weight |
| --- | --- |
| Sesame oil | 55 parts by weight |
| Glycerin fatty acid ester | 5 parts by weight |

Curcumin-containing soft capsules for foods were prepared using the above-listed ingredients according to a conventional method.

Example 7

Preparation of Curcumin-containing Crackers

| Curcumin | 1 part by weight |
| --- | --- |
| Plain flour | 120 parts by weight |
| Salt | 1 part by weight |
| Baking powder | 2 parts by weight |
| Butter | 30 parts by weight |
| Water | 40 parts by weight |

Curcumin-containing crackers were prepared using the above-listed ingredients according to a conventional method.

Example 8

Preparation of Curcumin-containing Udon Noodle

| Curcumin | 1 part by weight |
| --- | --- |
| Bread flour | 100 parts by weight |
| Plain flour | 100 parts by weight |
| Salt | 10 parts by weight |
| Water | 100 parts by weight |

Curcumin-containing udon noodle was prepared using the above-listed ingredients according to a conventional method.

Example 9

Preparation of Curcumin-containing Dressing

| Curcumin | 10 parts by weight |
| --- | --- |
| Olive oil | 80 parts by weight |
| Vinegar | 60 parts by weight |
| Salt | 3 parts by weight |
| Pepper | 1 part by weight |
| Lemon juice | 5 parts by weight |

Curcumin-containing dressing was prepared using the above-listed ingredients according to a conventional method.

We claim:

1. A method for reducing visceral fat, which comprises administering to a subject suffering from type-II diabetes mellitus, hyperinsulinemia, dyslipidemia, hypertension, and/or arteriosclerotic cardiovascular disease, a composition comprising at least one selected from the group consisting of curcumin and a curcuminoid as an active agent, with the intention of reducing visceral fat in said subject.

2. The method according to claim 1, wherein said composition is in the form of a food or a drink.

3. The method according to claim 1, wherein said composition is in the form of a pharmaceutical.

4. The method according to claim 1, wherein said subject is a domestic animal or pet.

* * * * *

UNITED STATES PATENT AND TRADEMARK OFFICE
CERTIFICATE OF CORRECTION

PATENT NO.         : 7,090,874 B2
APPLICATION NO. : 10/752643
DATED              : August 15, 2006
INVENTOR(S)       : Tatsumasa Mae et al.

It is certified that error appears in the above-identified patent and that said Letters Patent is hereby corrected as shown below:

On the title page item (75), replace "Yoshihiro Mimaki, Hachioji" with --Yoshihiro Mimaki, Tokyo--.

On the title page item (75), replace "Yutaka Sashida, Hachioji" with --Yutaka Sashida, Tokyo--.

Signed and Sealed this

Nineteenth Day of June, 2007

JON W. DUDAS
*Director of the United States Patent and Trademark Office*